(12) United States Patent
Taylor

(10) Patent No.: US 8,172,875 B2
(45) Date of Patent: *May 8, 2012

(54) VARIABLE LAMINOPLASTY IMPLANT

(75) Inventor: Brett Allison Taylor, Clayton, MO (US)

(73) Assignee: DePuy Spine, Inc., Raynham, MA (US)

( * ) Notice: Subject to any disclaimer, the term of this patent is extended or adjusted under 35 U.S.C. 154(b) by 1355 days.

This patent is subject to a terminal disclaimer.

(21) Appl. No.: 11/766,864

(22) Filed: Jun. 22, 2007

(65) Prior Publication Data

US 2008/0009865 A1 Jan. 10, 2008

Related U.S. Application Data

(63) Continuation of application No. 10/859,962, filed on Jun. 4, 2004, now Pat. No. 7,264,620.

(51) Int. Cl.
*A61B 17/70* (2006.01)

(52) U.S. Cl. ...................................... 606/246

(58) Field of Classification Search .................. 606/60, 606/246–250, 280–282, 70, 71; 623/17.11
See application file for complete search history.

(56) References Cited

U.S. PATENT DOCUMENTS

| | | | |
|---|---|---|---|
| 5,439,463 A | 8/1995 | Lin | |
| 5,470,333 A | 11/1995 | Ray | |
| 5,947,966 A * | 9/1999 | Drewry et al. | 606/252 |
| 5,980,572 A | 11/1999 | Kim et al. | |
| 6,050,997 A | 4/2000 | Mullane | |
| 6,080,157 A | 6/2000 | Cathro et al. | |
| 6,283,967 B1 | 9/2001 | Troxell et al. | |
| 6,306,137 B2 * | 10/2001 | Troxell | 606/252 |
| 6,635,087 B2 | 10/2003 | Angelucci et al. | |
| 6,660,007 B2 | 12/2003 | Khanna | |
| 6,712,852 B1 | 3/2004 | Chung et al. | |
| 6,776,800 B2 | 8/2004 | Boyer, II et al. | |
| 7,264,620 B2 | 9/2007 | Taylor | |
| 2002/0120335 A1 | 8/2002 | Angelucci et al. | |
| 2002/0120338 A1 | 8/2002 | Boyer et al. | |
| 2003/0045935 A1 | 3/2003 | Angelucci et al. | |
| 2003/0045936 A1 | 3/2003 | Angelucci et al. | |
| 2003/0125738 A1 | 7/2003 | Khanna | |
| 2003/0125740 A1 | 7/2003 | Khanna | |
| 2004/0030388 A1 * | 2/2004 | Null et al. | 623/17.11 |
| 2004/0064184 A1 | 4/2004 | Chung et al. | |
| 2004/0153155 A1 | 8/2004 | Chung et al. | |
| 2004/0210222 A1 | 10/2004 | Angelucci et al. | |

FOREIGN PATENT DOCUMENTS

| | | |
|---|---|---|
| EP | 01402830 A1 | 3/2004 |
| EP | 1420708 A1 | 5/2004 |
| EP | 1420709 A1 | 5/2004 |
| EP | 1427342 A1 | 6/2004 |
| JP | 2000-139970 A | 5/2000 |
| JP | 2003-79648 A | 10/2004 |
| WO | 9709940 | 3/1997 |
| WO | 2003101319 | 12/2003 |

* cited by examiner

*Primary Examiner* — Thomas C. Barrett
*Assistant Examiner* — Michael Araj
(74) *Attorney, Agent, or Firm* — Nutter McClennen & Fish LLP

(57) ABSTRACT

A vertebral implant comprising a first base configured for securing to a first cut portion of a vertebra, and second base configured for securing to a second cut portion of the vertebra. A connecting member is configured to associate the first and second bases at a preselected spacing from each other, and the implant is preferable adjustable to select the spacing.

18 Claims, 7 Drawing Sheets

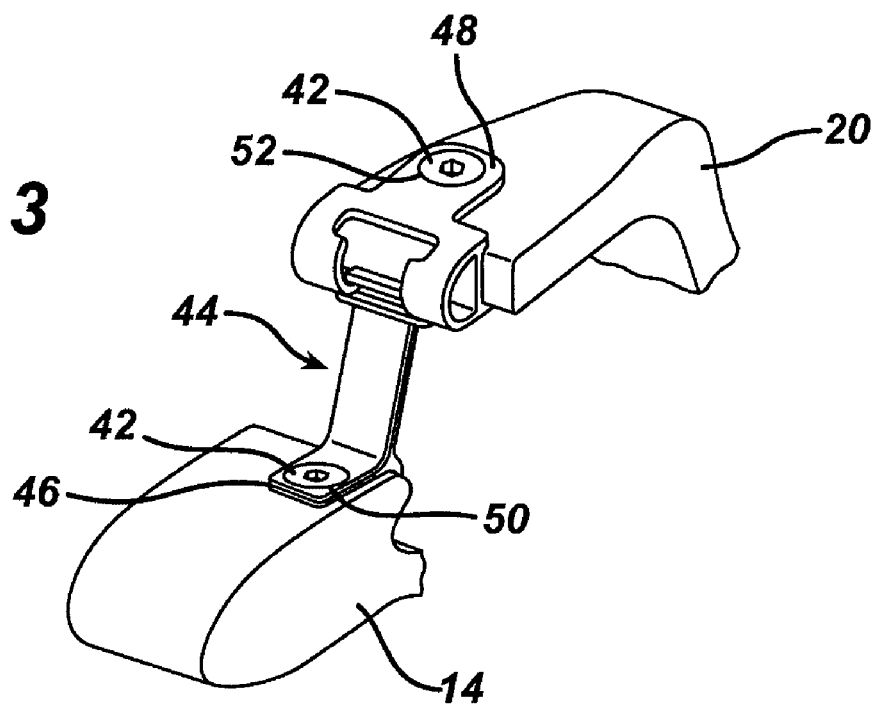
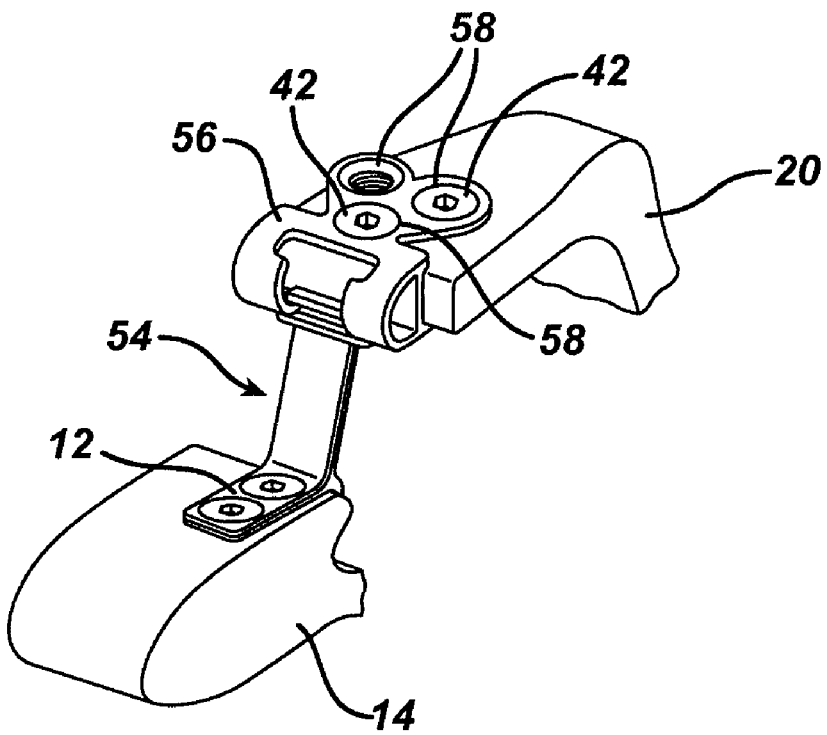

VARIABLE LAMINOPLASTY IMPLANT

CROSS-REFERENCE TO RELATED APPLICATIONS

The present application is a continuation of U.S. patent application Ser. No. 10/859,962 filed on Jun. 4, 2004 and entitled "Variable Laminoplasty Implant," which is hereby incorporated by reference in its entirety.

FIELD

The present application relates to an implant for bone surgery, and more specifically to a vertebral implant with an adjustable configuration.

BACKGROUND

In certain pathologies, the spinal canal extending through a patient's vertebrae is or becomes too narrow and constricts the spinal cord extending therethrough. The narrowing may be congenital, potentially affecting patients at any age. Narrowing can also be attributable to other causes, such as age, injury or removal of a spinal disk.

A condition associated with aging, for instance, is spondylolsis, in which intervertebral disc loose water and become less dense. These degenerative changes near the disk can cause an overgrowth of the bone, producing bony spurs called, "osteophytes" that can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebra to slip with respect to each other, also compressing the spinal cord. Instability between vertebra, such as caused by stretched and thickened ligaments' can also produce pressure on the spinal cord and nerve roots.

Myelopathy, or malfunction of the spinal cord, occurs due to its compression. The rubbing of the spine against the cord can also contribute to this condition, and the spinal cord compression can ultimately compromise the blood vessels feeding the spinal core, further aggravating they myelopathy.

Traditional procedures for decompressing the spinal cord include a laminectomy, in which the lamina and spinal processes are removed to expose the dura covering the spinal cord. Another known procedure is a laminoplasty, in which the lamina is lifted off the dura, but not completely removed. Typically, one side of the lamina is cut, while a partial cut is made on the other side to hinge the lamina away from the spinal cord to increase the size of the spinal canal. A laminoplasty plate is then screwed to a facet and to the hinged open lamina. The plate of an appropriate size is selected and bent to the desired shape and preferably has a plurality of screw holes. A strut of bone can be placed in the open portion within the lamina and the facet to help hold the open position of the lamina. Prior to the operation, the surgeon needs to measure the vertebra to determine the size of the plate necessary for implantation. At that point, a plate can be selected with the appropriate dimensions, and implanted at the site.

A laminoplasty implant is needed that preferably allows its size to be varied prior to implantation, preferably without changing its overall shape or configuration, so that a plate does not have to be custom selected and intensively shaped and formed prior to each surgery.

SUMMARY

The present invention relates to a bone implant, and more preferably a vertebral implant. The implant has first and second bases configured for securing two first and second cut portions, respectively, of a vertebra. A connecting member is configured for associating the first and second bases at a pre-selected spacing from each other. Most preferably, the implant is adjustable to select and set the spacing. In the preferred embodiment, the implant is a laminoplasty implant, and the first and second vertebral portions are a lateral mass, its articular mass, or its facet, or a portion of the lamina, and the second vertebral portion can comprise, for example, at least part of the lamina.

The first base is preferably in fixed association with the connecting member. One of the connecting members and second base comprises an adjustable member that is adjustable to select the spacing between the bases. The other of these portions of the implant can include a linking member that is associable with the adjustable member. The adjustable member preferably adjusts the length of the connecting member measured from the first base to a connection location at which the linking member is associated with the adjustable member. This length is preferably adjusted without changing the overall shape or configuration of the implant and preferably by changing the length of the connecting member without modifying the general shape of the bases or the size of the position of he bases in contact with the bone when implanted.

Also, the adjustable member can define a plurality of mating portions, with the linking member being associable selectively with at least one of the mating portions to select the connection location. The mating portions and linking member are preferably configured for pivotally associating the adjustable member and second base. The mating portions and linking member of the preferred embodiment are configured to be placed into the association at a first pivotal orientation with respect to each other, and for connecting the first and second bases secured to the cup portions in a second pivotal orientation between the linking member and mating portions or connecting member.

In one embodiment, the mating portions and/or linking member comprise at least one or more protrusions receivable in one or more notches of the other of these elements to associate the adjustable and linking members a protrusion can be selectively receivable in at least one of the notches for selecting the connection location. At least one of the notches and protrusions is preferably arcuate about axial direction measured with respect to the spinal column, such that the protrusion is received for sliding in the notch and in this manner pivoting of the connecting member with respect to the linking member without sliding in the notch can be restricted if desired. A loading opening can be provided, for example, between a pair of the protrusions to receive the notches of the adjustable member therein for associating the adjustable member and the linking member. The adjustable portion is preferably configured for severing a potion of the connecting member disposed beyond the selected connection location from the first base.

At least one of the bases can include a concave contacting surface that is configured for receiving the cut portions of the vertebra. At least one of the bases preferably includes a fastener mount portion configured to attach a bone fastener thereto to secure the base to the vertebra. The fastener mount portion can include a plurality of fastener mount portions that are disposed at different axial locations with respect to the spinal access. This allows attaching bone fasteners depending on the axial spacing between the first and second cut portions. A fastener can be mounted in the fastener mount portions, and in one embodiment the fastener is articularble and includes a universally pivotal head. The head is associable with a vertebra joining member, such as a rod and at least one other vertebra in the spinal column. A further fastener mount potion can be provided, such as in the connecting member, for securing a bone graft thereto. Once the first and second bases are secured to the first and second cut portions of the vertebra, the connecting member preferably fixes the association between the bases, thus fixing the distance therebetween and holding the lamina in a desired hinged position. In a preferred embodiment of an articularble fastener, the fastener has a bone fastener portion configured for fastening to a bone, a head configured for associating with the vertebra joining member, and a universal joint that pivotally associates the fastener portion with the head for relative universal pivoting therebetween. In one embodiment, a passage is cooperatively defined by the head and joint to permit access to the fastener portion to engage it directly with the driver. Thus, a driver can be used to screw the fastener portion into the bone prior to attaching to a rod, or other vertebrae joining member.

Consequently, an improved implant is provided that can be used in a laminoplasty procedure without requiring the intensive customization of a bone plate or the selection from a wide size variety of bone plates prior to implantation. Preferably the implants can be customized in situ to best fit the patients anatomy substantially reducing the amount of time and costs to perform the operation.

BRIEF DESCRIPTION OF THE DRAWINGS

Various exemplary embodiments disclosed herein will be more fully understood from the following detailed description taken in conjunction with the accompanying drawings, in which:

FIGS. 3 and 4 are perspective views of alternative embodiments of implants with different fastener mount portions;

DETAILED DESCRIPTION

Figure 1:
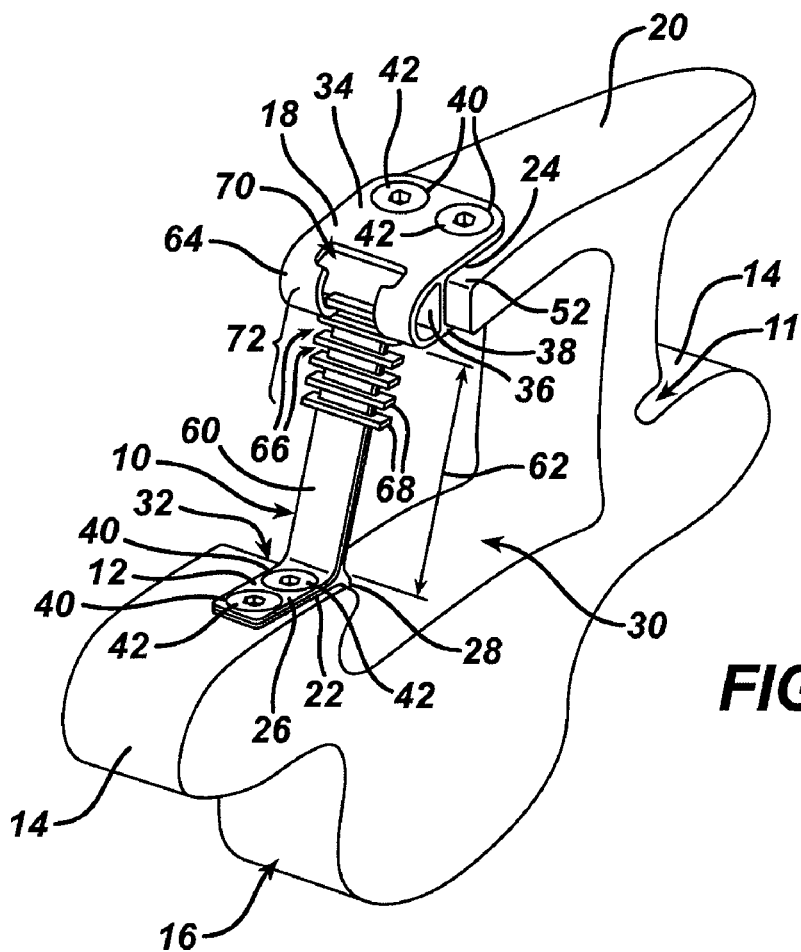
FIGS. 1 and 2 are perspective views of a laminoplasty implant constructed according to a preferred embodiment of the invention, adjusted to different lengths.

Referring to FIG. 1, in a preferred laminoplasty procedure, an osteotomy is performed in which a complete cut is made through vertebra 16, approximately between the lamina 20 and lateral mass 14, such as the articular mass or facet portion therof. A partial-depth cut 11 is made on the opposite lateral side, also approximately between the lamina 20 and other lateral mass 14. The lamina 20 is then hinged open about the partial cut 11 to increase the cross-sectional size of the spinal canal to decompress the spinal cord therein.

A preferred embodiment of a laminoplasty implant 10 includes a lateral base 12 that is configured for securing to a lateral mass 14 of a vertebra 16. A lamina base 18 is configured for securing to a portion of a lamina 20 that has been cut and hinged away from the lateral mass 14. For alternative surgical procedures, the base can be configured for securing to different parts of the vertebra, a differently prepared vertebra, or to different bones, as desired.

Preferably, one or both bases 12,18 have concave contacting surfaces 22,24 that are configured for receiving the cut portions of the vertebra 16, such as at the lateral mass 14 and lamina 20. The lateral base 12 of the embodiment shown has an outside portion 26 that is preferably placed against the posterior surface of the lateral mass 14 outside the spinal canal 30, and against an inside portion 28 that is preferably placed against a wall of the vertebrae at an angle to the position facet surface at the cut 32 location, preferably in the interior of the spinal canal 30. Together, the outside and inside portions 26,28 of the lateral base 12 define the concave surface 22 for receiving and capturing the cut portion of the lateral facet 14. The individual surfaces of the outside and inside portions 26,28 can also be concave, preferably by a slight amount.

In the embodiment shown, the angle between the outside and inside potions 26,28 at the concave surface is about a right angle, but can be varied depending on the location of the implantation and the angle of the cut that is made. Preferably, the angle is between about 30.degree. and 150.degree., and more preferably between about 60.degree. and 100.degree. In one embodiment, the angle can be up to about 180.degree., such as by employing an intermediate portion to connect the outside and inside portions. The inside portion 28 can be constructed as a lip to capture the edge of the lateral mass 14 at the cut, to assist in the proper placement of the implant 10 and prevent or restrict movement thereof after implantaion.

The lamina base 18 also preferably has an outside portion 34, which is preferably placed against the posterior surface of the lamina 20 outside the spinal canal 30. An intermediate portion 36 is configured and disposed for placement against a narrow edge of the lamina 20, and an inside portion 38 is placed against an anterior surface of the lamina 20 inside the spinal canal 30. Together, the outside, intermediate, and inside portions 34,36,38 of the lamina base 18 define the concave surface 24 for receiving and capturing the cut portion of the lamina 20, preferably surrounding the cut portion of the lamina 20. The inside portion 38 can be configured as a lip to help prevent pivoting of the lamina 20 tending to close the spinal canal 30 prior to the bone healing.

The angle between the outside and intermediate portions 34,36 in the preferred embodiment and between the intermediate and inside potions 36,38 at the concave surface are about right angles, but can be varied depending on the location of the implantation and the angle of the cut that is made. In one embodiment, only two angled portions are used, such as by providing a lip to capture the edge of the cut lamina, as is shown for the lateral base 12. The angle between the outside and inside portions is preferably about 180.degree., but can alternatively be as low as about 30.degree., more preferably as low as about 60.degree., and most preferably as low as about 90.degree. The concave surface 24 captures the edge of the lamina 20 at the cut, to assist in the proper placement of the implant 10.

The bases 14,18 preferably include fastener mount portions 40 configured for attaching a bone fastener thereto. If bone screws 42 are to be used, then the fastener mount portions can define suitable openings for receiving and fastening the bone screws 42. The fastener mount portions 40 are preferably disposed for accessing and inserting the fasteners 42 from the outside of the bone, to facilitate implantation.

The lateral base 12 shown has two fastener mount portions 40 aligned laterally with respect to each other. The lamina base 18 shown, on the other hand, has two fastener mount portions 40 disposed axially with respect to each other. The position of the fastener mount portions 40 can be varied according to the bone available at the implantation site. For instance, the implant 44 of FIG. 3 has facet and lamina bases 46,48, each with a fastener mount portion 50,52 configured to attach a single bone screw 42. The implant 54 of FIG. 4, however, has a lamina base 56 with fastener mount portions 58 configured for receiving and attaching up to three bone screws 42. Alternative bases can secure to other numbers of fasteners in other arrangements. Similar fastener mount portion arrangements can be used for the lateral base.

The fastener mount portions of implant 54, shown in FIG. 4, has three fastener mount portions 58 oriented generally along the apices of a triangle. Two of the fastener mount portions 58 are disposed generally at a same lateral location, and at least two of the three are preferably disposed at different axial locations along the spinal axis when implanted. Since the vertebral laminae are displaced downwardly in an axial direction with respect to the facets of the same vertebrae, axially displaced fastener mount portions, such as in lamina base 56 in FIG. 4 and lamina base 18 in FIG. 1, can help ensure that at least one or more of the fastener mount portion 40,58 is disposed over bone into which a fastener can be placed.

As shown in FIG. 4, the upper fastener mount portion 58 is empty, as it is not completely over lamina bone. On the other hand, the other two fastener mount portions 58 are fully disposed over bone, and each has a bone screw 42 secured therethrough. The leftmost fastener mount portion 58, disposed closest to the lateral base 12, is preferably disposed axially between the other two fastener mount portions 58 in a position likely to always be able to engage the bone with a fastener. If the implant 54 were used on the right side of a vertebra, instead of on the left side as shown, the other of the two fastener mount portions 58 that are is a close axial position would be over bone and used for securing a fastener, while the fastener mount portion that is shown with a bone screw 42 in FIG. 4 would be empty. In an alternative embodiment, the triangle may be reversed, with a pair of fastener mount portions provided towards the lateral base, and a single fastener mount portion provided further therefrom than the other two. An alternative embodiment has an asymmetrical arrangement of fastener mount portions, and one embodiment has two positioned along a line that is diagonal to the lateral direction between the facet and lamina bases.

Referring again to FIG. 1, implant 10 has a connecting member 60 that associated the facet and lamina bases 12,18 at a preselected spacing 62 from each other. The spacing 62 is selected to determine the hinged position in which the cut lamina will be maintained when the surgery is complete. The connecting member 60 preferably acts as a strut holding the bases 12,18 apart.

The preferred connecting member 60 and/or its association with at least one of the bases 12,18 is adjustable for selecting the desired spacing 62. In the preferred embodiment, one of the bases 12,18, preferably the lateral base 12, is in fixed association, and preferably integral with or of unitary construction with the connecting member 60. The other base, preferably the lamina base 18, has a linking member 64 that is associable with the connecting member 60. The preferred linking member 64 has at least one protrusion, such as parallel D-rings, that is associable with any of a plurality of notches 66 defined between ledges 68 on the connecting member 60 to select a location for the connection between a notch 66 and the D-ring.

Prior completing the implantation, such as after the lamina base 18 is secured to the cut lamina 20 but before the lateral base 12 is secured to the lateral mass 14, at least one of the ledges 68 of the connecting member 60 is inserted into a loading opening, such as a slot 70 defined in the linking member 64 and extending into the facing D-rings, which slot 70 preferably has a larger cross-section than the cross-section of the ledges 68 along a plane parallel to the notches 66.

Once a ledge 68 is placed within the slot 70, the mated connecting member 60 and linking member 64 are pivotally associated, and the connecting member 60 can be pivoted about an axis that is preferably generally parallel to the spinal axis to place the lateral base 12 against the vertebra lateral mass 14, where it can be secured. When both bases 12,18 are engaged with each other and secured to the respective bone portions, the connecting member 60 preferably maintains the bases 12,18 in fixed association with each other, preferably substantially preventing movement between the bases 12,18.

Figure 2:
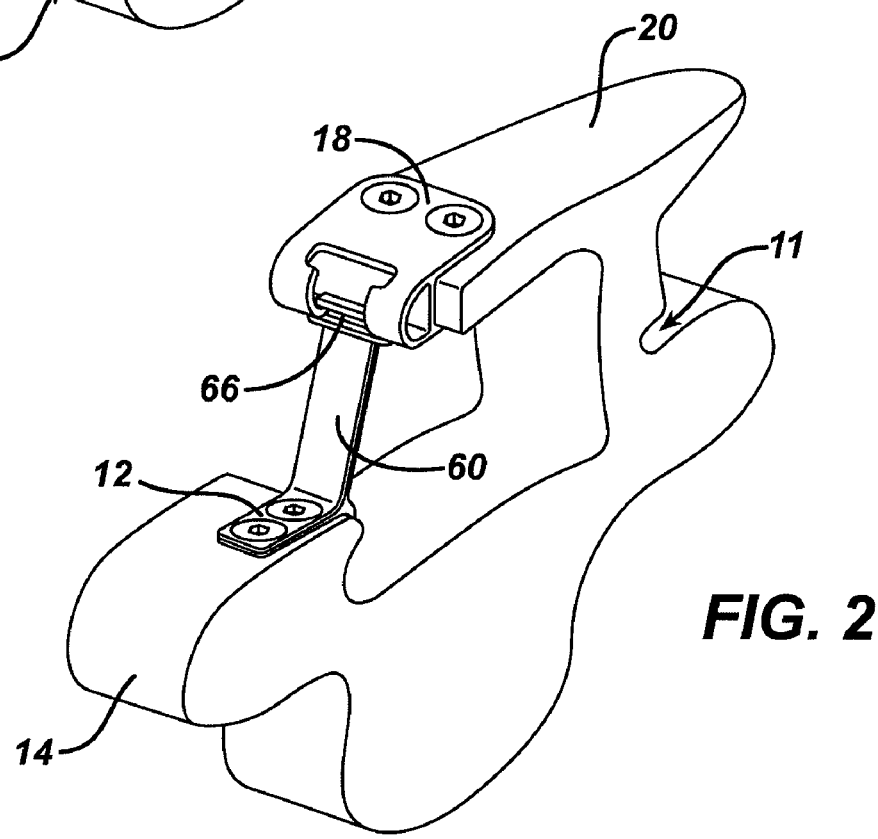

The connecting member 60 is adjustable in length, and preferably comprises an adjustable member 72, which includes the notched 66 and ledges 68. The adjustable member 72 is adjustable to adjust a length of the connecting member 60 and thus the spacing 62. By selecting the notch 66 to be mated with the linking member 64 D-rings, the length of the connecting member 60 can be incrementally adjusted. Once the anatomy of the vertebra is measured and preferably verified by mating the connecting member 60 with the lamina base 14 and pivoting the connecting member 60 and lateral base 12 portion to contact the lateral mass 14, the connecting member 60 can be separated from the lamina base 18. The adjustable member 72 of the connecting member 60 can then be clipped on the opposite side of the desired notch 66 from the lateral base 12 to shorten the connecting member 60 and eliminate unneeded material. FIG. 2 shows an implantation of the implant 10 with the connecting member adjusted and clipped to a shorter length than in FIG. 1, thus fixing the lamina 20 at a smaller open hinged angle than in FIG. 1. The shorter arrangement of FIG. 2 can also be used for smaller vertebrae.

Figure 5:
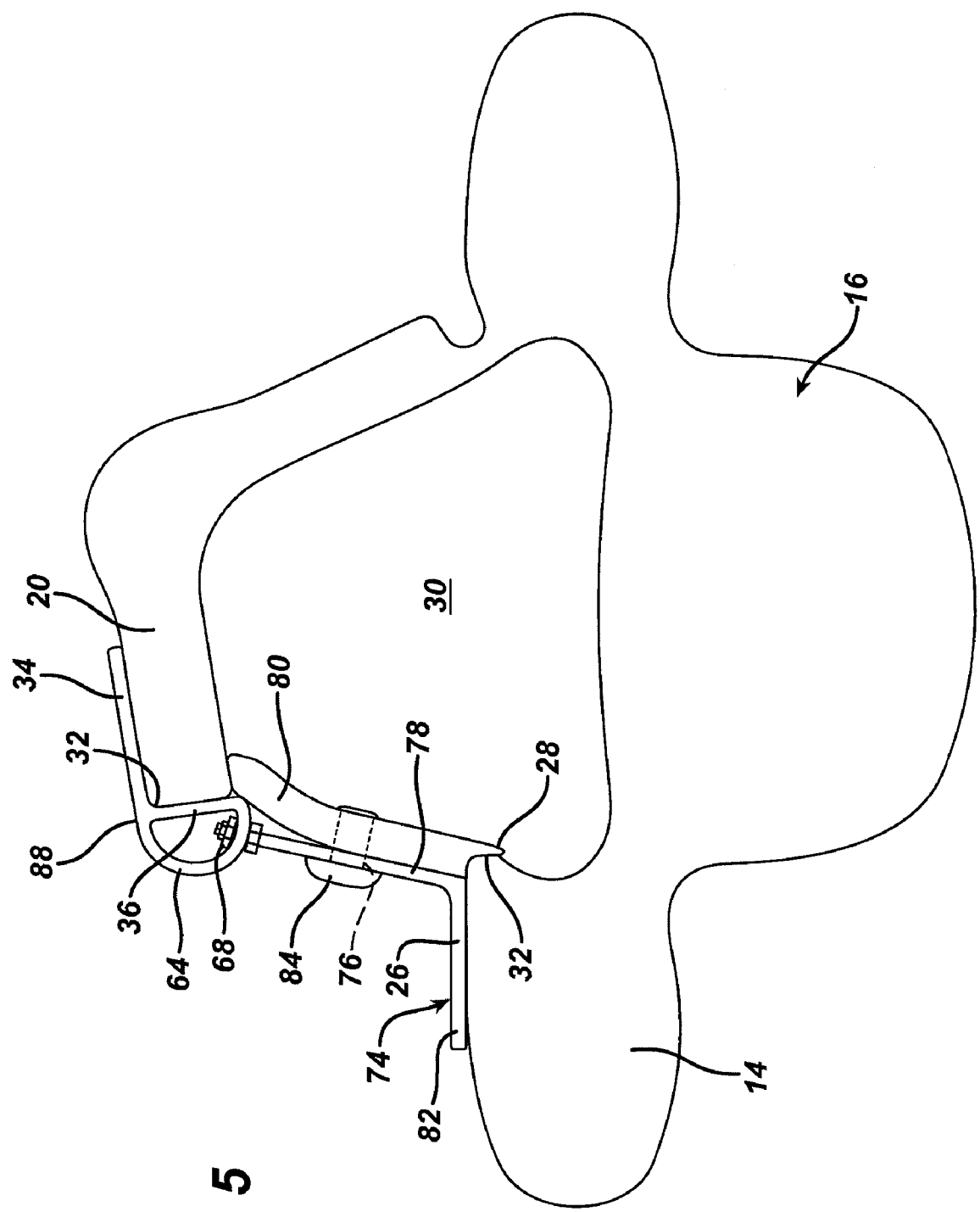
FIGS. 5 and 6 are a bottom view and a perspective rear view of another embodiment of an implant.
Figure 6:
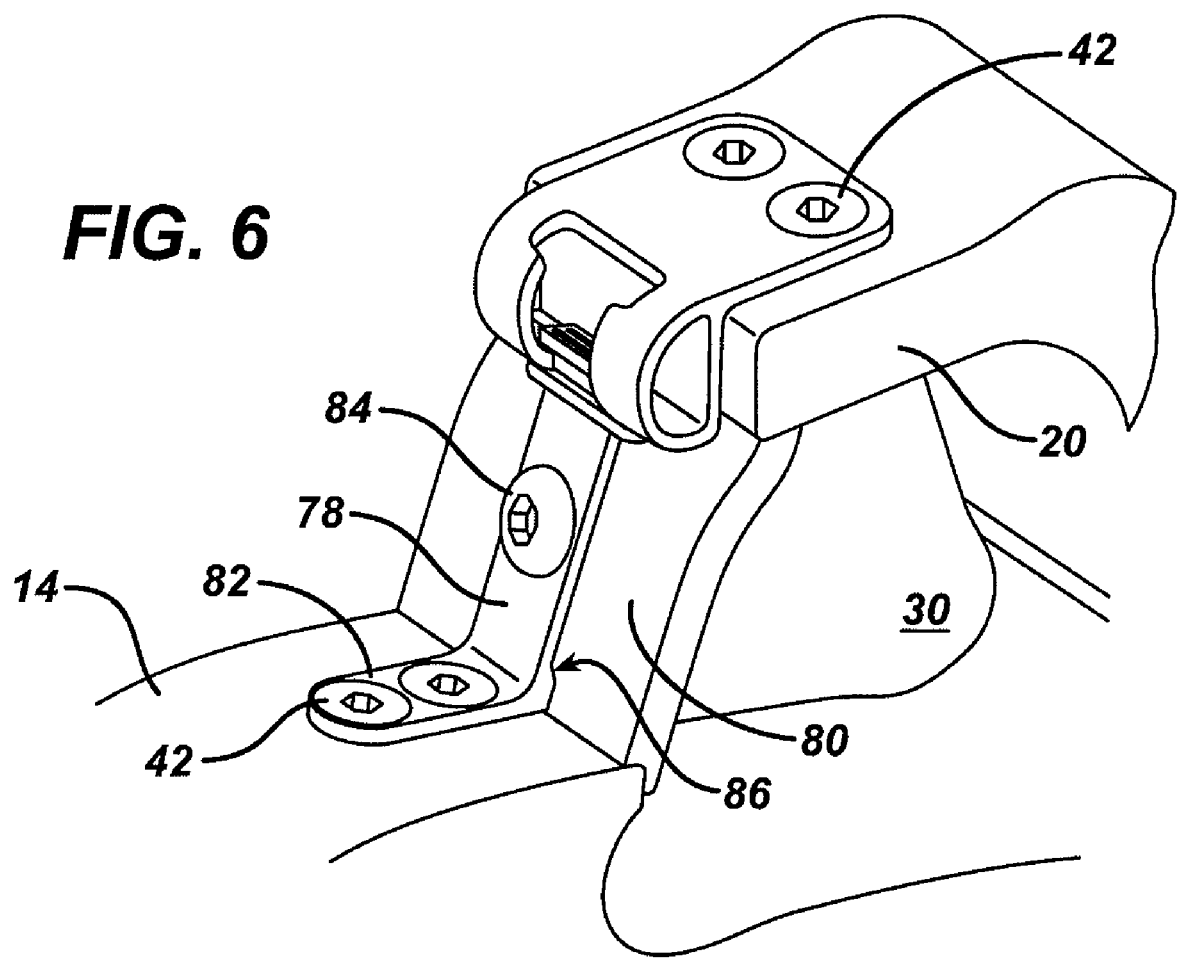

Referring to FIGS. 5 and 6, another implant 74 embodiment is shown with a fastener mount portion 76, which is preferably associated with connecting member 78 and faces the spinal canal 30. Fastener mount portion 76 is preferably positioned and configured for securing a bone graft fragment 80 to help support the hinged lamina 20 in the open position, and ultimately for fusing with the vertebral bone when the vertebra heals. A fastener, such as a bone screw 84 is fastened through the fastener mount portion 76 to the one fragment 80.

In the embodiment shown, the connecting member 78 is substantially straight. Alternatively, the connecting member can be curved, preferably bowed outwardly from the spinal canal to increase its expanded cross-sectional size.

The bone fragment 80 is shaped to preferably contact both sides of the cut 32 in the vertebra 16. The bone fragment 80 is preferably also provided with a notch 86 to receive the inside portion 28 of lateral base 82 to extend around the cut portion of the lateral mass 14. Although a similar notch can be provided for the lamina base 88, the lamina base 88 of this embodiment does not have a third portion that extends inside the spinal canal 30. As shown in FIG. 5, the ledges are arcuately curved about an axial direction with respect to the spinal column, preferably following the curved shape of the D-rings of linking member 64 and further controlling the relative orientation between the connecting member 78 and the linking portion 64.

Figure 7:
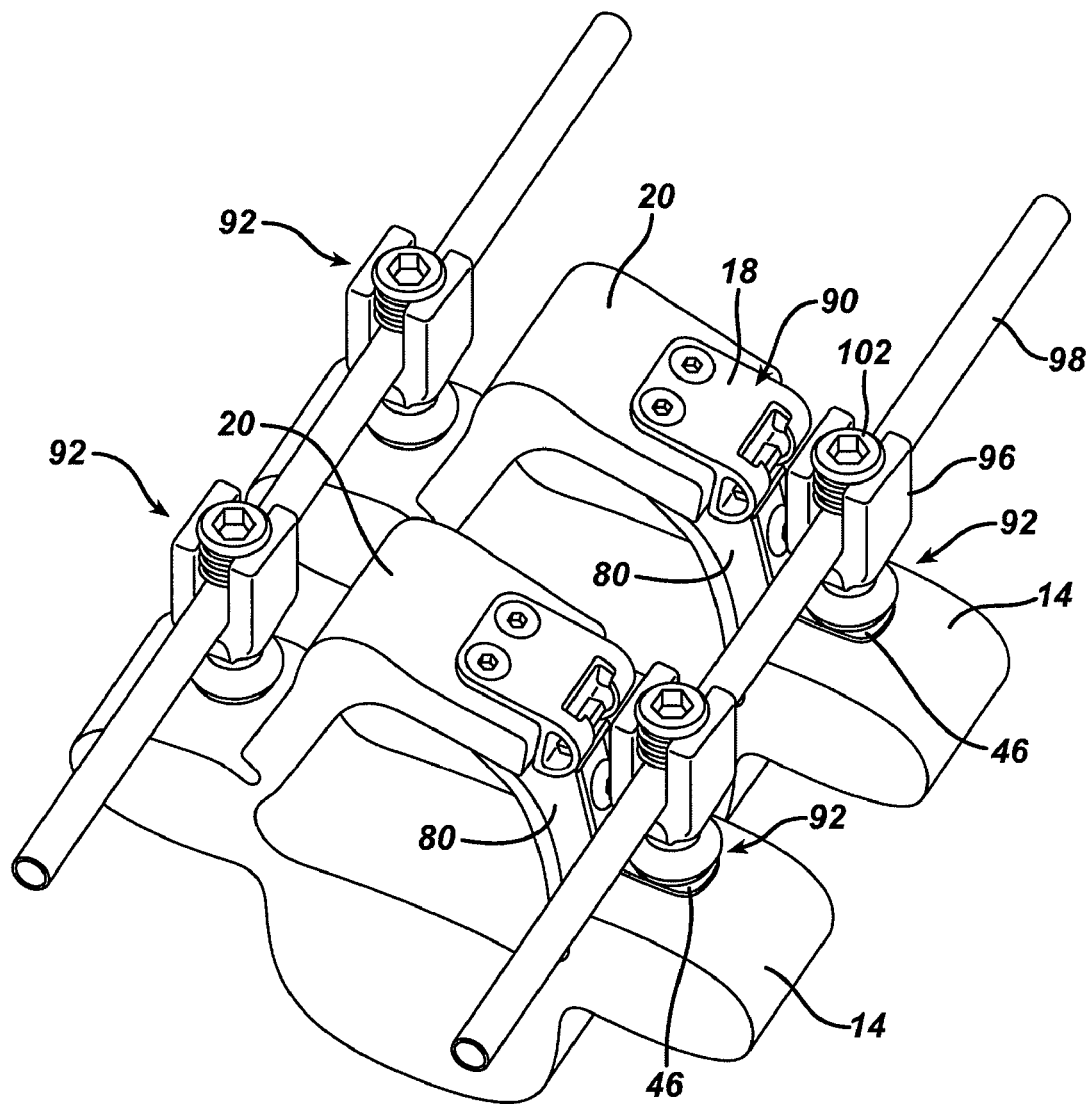
FIGS. 7 and 8 are a perspective and axial view of an implant fixed with other vertebrae.

As shown in FIG. 7, an implant embodiment 90 has a lateral base 46 that is secured to lateral mass 14 by an articulated bone fastener 92, which is itself secured to at least one adjacent vertebra 16. Fastener 92 comprises a fastener portion 94, which is preferably a bone screw portion fastened to the vertebra 16, and a head 96 that is configured for associating with a vertebra joining member, such as a rod 98. A locking mechanism, such as a set screw 102, preferably locks the rod 98 to the head 96. A joint 100, which is preferably substantially universally pivotable and also preferably rotatably, pivotally associates the head 96 with the fastener portion 94.

Figure 8:
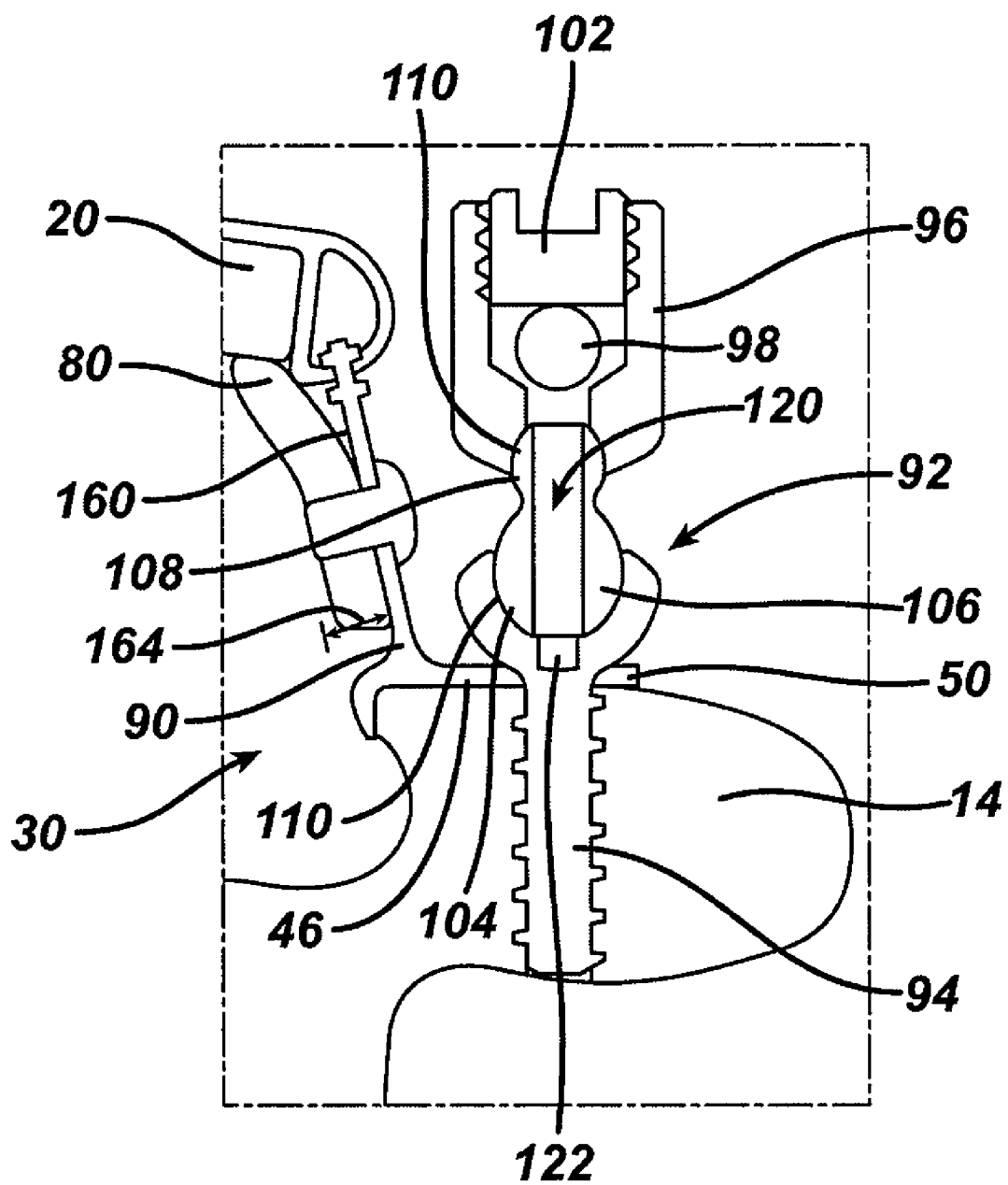

As shown in FIG. 8, an embodiment of the joint 100 includes a link 104 configured with two spherical portions 106,108, preferably of different sizes. Each spherical portion 106,108 is received in a socket 110 of the head 96 or the fastener portion 94. The sockets 110 preferably extend more than half way around the spherical portions 106,108 to retain the spherical portions 106108 therein. A double ball and socket joint is thus provided, preferably allowing rotation, and most preferably unlimited rotation, at least about the axis of the head 96 or fastener portion 94. Pivoting is preferably allowed through an arc of between about 10.degree. and 80.degree., and more preferably between about 20.degree. and 70.degree., preferably in any direction about the spherical portions 106,108.

A passage 120 is preferably defined cooperatively by aligned openings in the head 96 and joint 100 configured to receive a driver, such as a screw driver, to engage directly with the fastener portion 49 to secure it to the bone. The passage 120, preferably is aligned with a driver receptacle 122 in the fastener portion 94.

The articulated fasteners 92 thus allow other vertebrae to support each other and can be useful where vertebrae are to be fused. As shown in FIG. 7, a similar arrangement of articulated fasteners 92 and rods 98 can also be employed on the opposite facets 14 to improve support and possibly fixation with other vertebrae.

Figure 11:
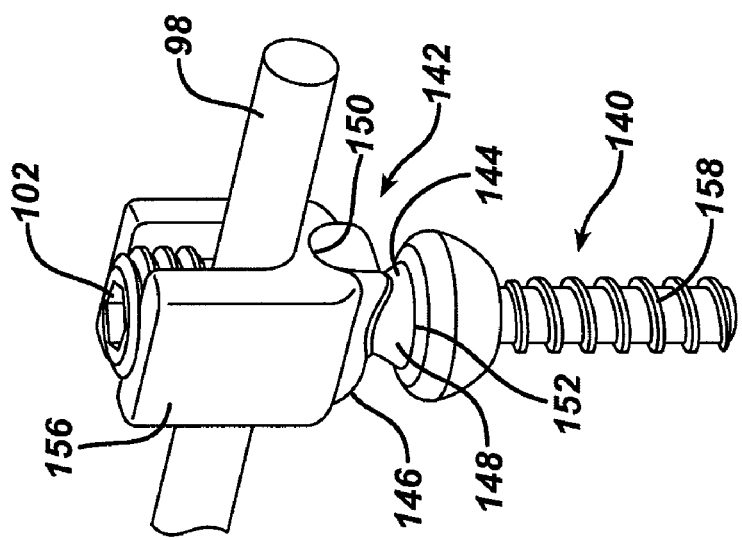
FIG. 11 is a perspective view of another embodiment of an articulated fastener.
Figure 10:
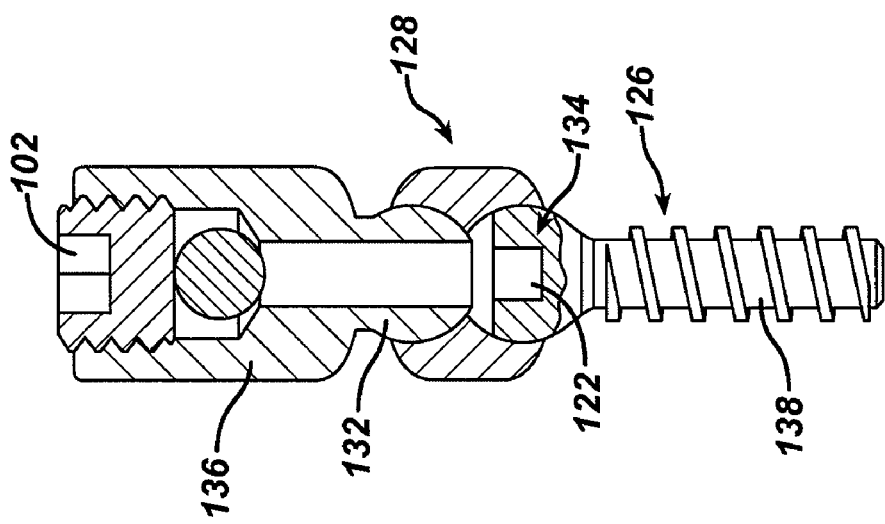
FIGS. 9 and 10 are cross-sectional views of other embodiments of inventive universally pivotable screws.
Figure 9:
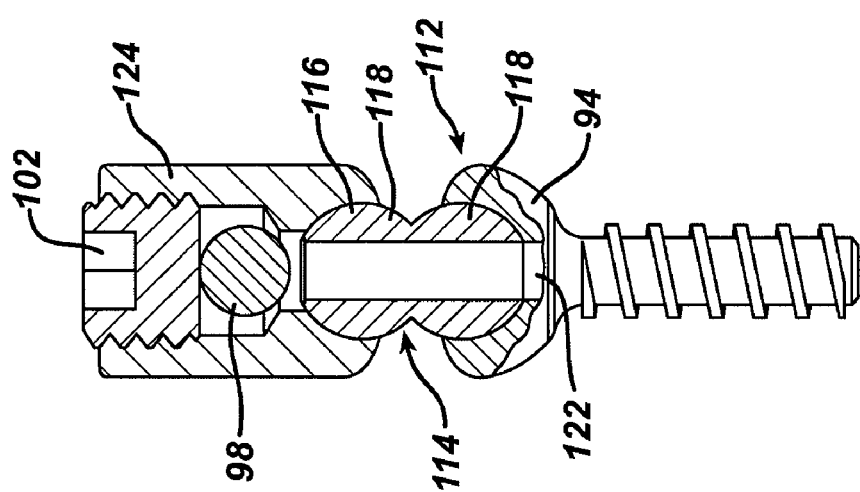

Another embodiment of a pivoted fastener 112 is shown in FIG. 9, in which a double ball and socket joint 114 includes a link 116 with two spherical portions 118 associated with head 124 and fastener portion 94. The joint 128 articulated fastener 126 of FIG. 10 includes a double-socket member 130 that receives spherical portions 132,134, which are respectively integral or unitary with the head 136 and fastener portion 138. The articulated fastener 140 of FIG. 11 has a joint 142 with a link 144 that has a cylindrical portion 146 associated with a spherical portion 148, which are received in complementary sockets 150, 152 in head 156 and fastener portion 158, respectively. Although the spherical portion 148 can rotate about an axis joining the fastener portion 158 and head 156, the cylindrical portion 146 is restricted against such rotation.

Referring again to FIG. 8, a unitary facet-base/connecting-member portion has the connecting member 160 offset from the interior edge of the lateral base 46, which is disposed closest to the spinal canal 30, by an offset amount 164, measured laterally in this embodiment. This offset 146 is preferably of similar or greater thickness as the thickness of the bone graft 80. In an alternative embodiment, greater or lesser offsets can be provided, including substantially no offset at all. In embodiments without a bone graft, the offset 154 can provide additional room for the expanding spinal cord. Also, the connecting member preferably extends at an angle of between about 100.degree. and 140.degree. from the lateral base.

The preferred materials for use in the embodiments of the implants of the present invention include titanium, PEEK (polyetheretherketone) and absorbable materials such as a polylactic or polyglycolic acid material. Other suitable materials may alternatively be used. The preferred spacing 62 provided by the connecting member 60 is between about 5 mm and 30 mm, depending on the location in the spine in which it is desired to be employed. For example, cervical implants will typically be between about 10 mm and 20 mm, while lumbar implants will typically be between about 20 mm and 30 mm. The bone screw diameters can also vary according to the size of the implant and the implant location, and typically vary between about 3 mm and 6 mm, with a length of about 8 mm to 20 mm.

While illustrative embodiments of the invention are disclosed herein, it will be appreciated that numerous modifications and other embodiments may be devised by those skilled in the art. Therefore, it will be understood that the appended claims are intended to cover all such modifications and embodiments that come within the spirit and scope of the present invention

What is claimed is:

1. A vertebral implant, comprising:
a first base having a fastener mount portion configured to receive a fastener for coupling the first base to a first cut portion of a vertebra;
a second base having a fastener mount portion configured to receive a fastener for coupling the second base to a second cut portion of the vertebra; and
an elongate connecting member extending from the second base and adapted to couple to the first base, wherein the connecting member has one or more transverse ledges formed thereon and spaced axially along the connecting member at a plurality of positions, such that the connecting member is adapted to couple to the first base via the transverse ledges at one of the plurality of positions so as to maintain the first and second cut portions of the vertebra in a selected hinged position.

2. The implant of claim 1, wherein the first base includes a linking member adapted to receive the connecting member.

3. The implant of claim 2, wherein the linking member comprises at least one D-ring, and wherein the connecting member includes a plurality of ledges that are matable to the at least one D-ring.

4. The implant of claim 1, wherein the connecting member includes an adjustable member formed on a terminal end thereof and having a length adapted to be adjusted.

5. The implant of claim 1, wherein the first and second bases includes concave surfaces adapted to be positioned against the first and second cut portions.

6. The implant of claim 1, further comprising a fastener mount portion formed in the connecting portion and adapted to receive a fastener.

7. The implant of claim 1, further comprising a fastener fastenable in the fastener mount portion formed in at least one of the first and second bases.

8. The implant of claim 7, wherein the fastener includes a universally pivotable head that is associable with a vertebrae joining member that is configured for attaching to at least one other vertebra in a spinal column.

9. A vertebral implant system, comprising:
a first base having at least one opening formed therein;
a first fastener adapted to be disposed through the at least one opening in the first base to mate the first base to a first cut portion of a vertebra;
a second base having at least one opening formed therein and having a linking member integrally formed thereon;
a second fastener adapted to be disposed through the at least one opening in the second base to mate the second base to a second cut portion of a vertebra; and
a connecting member integrally formed with the first base and adapted to extend between the first and second bases to maintain the first and second cut portions of the vertebra in a plurality of preselected hinged positions wherein the linking member is adapted to receive the connecting member.

10. The implant system of claim 9, wherein the linking member comprises at least one D-ring, and wherein the connecting member includes a plurality of ledges that are matable to the at least one D-ring.

11. The implant system of claim 9, wherein the connecting member includes an adjustable member formed on a terminal end thereof and having a length adapted to be adjusted.

12. The implant system of claim 9, wherein the first and second bases includes concave surfaces adapted to be positioned against the first and second cut portions.

13. The implant system of claim 9, further comprising a fastener mount portion formed in the connecting portion and adapted to receive a third fastener.

14. The implant system of claim 9, wherein the first and second fasteners include a universally pivotable head that is associable with a vertebrae joining member.

15. A method of increasing the size of the spinal canal, comprising:
attaching first and second bases to first and second cut portions of a vertebra such that a connecting member coupled to the first and second bases extends between the first and second cut portions of the vertebra; and
adjusting a distance between the first and second cut portions by repositioning the connecting member relative to one of the first and second bases to thereby increase the size of a spinal canal of the vertebra, wherein adjusting a distance between the first and second cut portions by repositioning the connecting member comprises positioning an adjustable member formed on a terminal end of the connecting member in one of a plurality of positions relative to a linking member formed on one of the first and second bases.

16. The method of claim 15, wherein attaching first and second bases to first and second cut portions of a vertebra comprises inserting first and second fasteners through a fastener mount portion formed in the first and second bases to implant bone-engaging portions of the first and second fasteners in the first and second cut portions of the vertebra.

17. The method of claim 15, wherein the first cut portion includes a portion of a lateral mass of the vertebrae, and the second cut portion includes a portion of a lamina of the vertebrae.

18. The method of claim 15, furthering comprising removing a portion of the connecting member to adjust a length of the connecting member.

* * * * *